US007217523B2

(12) United States Patent
Wagner

(10) Patent No.: US 7,217,523 B2
(45) Date of Patent: May 15, 2007

(54) NUCLEOSIDE PHOSPHORAMIDATES AND NUCLEOSIDE PHOSPHORAMIDASES

(75) Inventor: Carston R. Wagner, St. Paul, MN (US)

(73) Assignee: Regents of the University of Minnesota, Saint Paul, MN (US)

( * ) Notice: Subject to any disclaimer, the term of this patent is extended or adjusted under 35 U.S.C. 154(b) by 0 days.

(21) Appl. No.: 11/174,121

(22) Filed: Jul. 1, 2005

(65) Prior Publication Data

US 2006/0014193 A1 Jan. 19, 2006

Related U.S. Application Data

(60) Provisional application No. 60/584,958, filed on Jul. 2, 2004.

(51) Int. Cl.
 C12Q 1/68 (2006.01)
 F01N 3/10 (2006.01)
 G01N 33/573 (2006.01)
 G07N 33/53 (2006.01)
 C12N 11/04 (2006.01)
 C07K 14/00 (2006.01)
 C07H 21/04 (2006.01)

(52) U.S. Cl. .......................... 435/6; 422/173; 435/7.4; 435/7.6; 435/7.72; 435/183; 530/350; 536/23.2; 536/23.4

(58) Field of Classification Search ..................... None
 See application file for complete search history.

(56) References Cited

U.S. PATENT DOCUMENTS

| 4,683,195 | A | 7/1987 | Mullis et al. |
| 4,683,202 | A | 7/1987 | Mullis |
| 4,800,159 | A | 1/1989 | Mullis et al. |
| 4,965,188 | A | 10/1990 | Mullis et al. |
| 6,396,057 | B1 | 5/2002 | Jarrell et al. |
| 6,475,985 | B1 | 11/2002 | Wagner et al. |
| 2005/0124023 | A1 * | 6/2005 | Kellner et al. ............... 435/21 |

FOREIGN PATENT DOCUMENTS

WO   WO 96/40968   12/1996

OTHER PUBLICATIONS

Kuba et al. (1994) Nucleoside monophosphoramidate hydrolase from rat liver: purification and characterization. International Journal of Biochemistry. 26(2): 235-245.*
Bieganowski et al. (2002) Adenosine monophosphoramidase activity of Hint and Hnt1 supports function of Kin28, Ccl1, and Tfb3. Journal of Biological Chemistry. 277(13):10852-10860.*
Chang et al. (2001) Amino acid phosphoramidate monoesters of 3'-azido-3'-deoxythymidine: relationship between antiviral potency and intracellular metabolism. Journal of Medicinal Chemistry. 44: 223-231.*

Saboulard et al. (1999) Characterization of the activation pathway of phosphoramidate triester prodrugs of stavudine and zidovudine. Molecular Pharmacology. 56: 693-704.*
Meyers et al. (2000) Synthesis and biological activity of novel 5-fluoro-2'-deoxyuridine phosphoramidate prodrugs. Journal of Medicinal Chemistry. 43: 4313-4318.*
Dudkin et al. (1971) Hydrolysis of uridine-5' N-aryl and N-alkyl phosphoramidates by ribonucleoside-5' phosphoramidase. FEBS Letters. 16(1): 48-50.*
Abraham et al. (1996) Synthesis and biological activity of aromatic amino acid phosphoramidates of 5-fluoro-2'-deoxyuridine and 1-b-arabinofuranosylcytosine: evidence of phosphoramidase activity. Journal of Medicinal Chemistry. 39: 4569-4575.*
GenBank Accession No. Z74173. (2005) Accessed Jun. 2, 2006. 2 pages.*
GenBank Accession No. Y11175. (submitted 1997). Accessed Jun. 2, 2006. 2 pages.*
GenBank Accession No. BC007090 dated Jul. 15, 2006, 3 pages.
GenBank Accession No. BC070415 dated Jul. 15, 2006, 3 pages.
GenBank Accession No. NM_138571 dated Mar. 23, 2006, 3 pages.
GenBank Accession No. Y11175 dated May 9, 2003, 2 pages.
GenBank Accession No. Z74173 dated Apr. 18, 2005, 2 pages.
GenBank Accession No. AY486461 dated Jan. 15, 2004, 2 pages.
GenBank Accession No. AY486460 dated Jan. 15, 2004, 2 pages.
Abraham et al., "Synthesis and Biological Activity of Aromatic Amino Acid Phosphoramidates of 5-Fluoro-2'-deoxyuridine and 1-β-Arabinofuranosylcytosine: Evidence of Phosphoramidase Activity," *J. Med. Chem.*, 1996, 39:4569-4575.
Avdulov et al., "Activation of translation complex of eIF4F is essential for the genesis and maintenance of the malignant phenotype in human mammary epithelial cells," *Cancer Cell*, 2004, 5:553-563.
Altschul et al., "Gapped BLAST and PSI-BLAST: a new generation of protein database search programs," *Nucl. Acids Res.*, 1997, 25:3389-3402.
Bieganowski et al., "Adenosine Monophosphoramidase Activity of Hint and Hnt1 Supports Function of Kin28, Ccl1, and Tfb3," *J. Biol. Chem.*, 2002, 277(13):10852-10860.
Bjornsti and Houghton, "Lost in translation: Dysregulation of cap-dependent translation and cancer," *Cancer Cell*, 2004, 5:519-523.
Chang et al., "Amino Acid Phosphoramidate Monoesters of 3'-Azido-3'-deoxythymidine: Relationship between Antiviral Potency and Intracellular Metabolism," *J. Med. Chem.*, 2001, 44(2):223-231.

(Continued)

*Primary Examiner*—Jeffrey Fredman
*Assistant Examiner*—Angela Bertagna
(74) *Attorney, Agent, or Firm*—Fish & Richardson P.C.

(57) ABSTRACT

The invention provides isolated nucleic acid sequences encoding polypeptides having nucleoside phosphoramidase activity, and methods of screening for nucleoside phosphoramidate compounds that are cleaved by a phosphoramidase or for phosphoramidases that are able to cleave phosphoramidate compounds. The invention also provides methods of delivering a nucleoside monophosphate.

8 Claims, 5 Drawing Sheets

OTHER PUBLICATIONS

Chou et al., "$^{31}$P NMR and Genetic Analysis Establish hinT as the Only *Escherichia coli* Purine Nucleoside Phosphoramidase and as Essential for Growth under High Salt Conditions," *J. Biol. Chem.*, 2005, 280(15):15356-15361.

Datsenko and Wanner, "One-step inactivation of chromosomal genes in *Escherichia coli* K-12 using PCR products," *Proc. Natl. Acad. Sci. USA*, 2000, 97(12):6640-6645.

Schwartz and Dayhoff, "Matrices for Detecting Distant Relationships," *Atlas of Protein Sequence and Structure*, 1978, vol. 5, Suppl. 3, pp. 353-358.

Dudkin et al., "Hydrolysis of Uridine-5' *N*-ARYL and *N*-ALKYL Phosphoramidates by Ribonucleoside-5' Phosphoramidase," *FEBS Letters*, 1971, 16(1):48-50.

Gilmour et al., "Isolation, cloning and characterization of a low-molecular-mass purine nucleoside-and nucleotide-binding protein," *Biochem. J.*, 1997, 326:471-77.

Hanahan, "Studies on Transformation of *Escherichia coli* with Plasmids," *J. Mol. Biol.*, 1983, 166:557-580.

Krakowiak et al., "Biochemical, Crystallographic, and Mutagenic Characterization of Hint, the AMP-Lysine Hydrolase, with Novel Substrates and Inhibitors," *J. Biol. Chem.*, 2004, 279(18):18711-18716.

Kuba et al., "Nucleoside Monophosphoramidate Hydrolase from Rat Liver: Purification and Characterization," *Int. J. Biochem.*, 1994, 26(2):235-245.

Kunkel et al., "Rapid and Efficient Site-Specific Mutagenesis without Phenotypic Selection," *Meth. Enzymol.*, 1987, 154:367-382.

Landegren et al., "A Ligase-Mediated Gene Detection Technique," *Science*, 1988, 241:1077-1080.

Meyers et al., "Synthesis and Biological Activity of Novel 5-Fluoro-2'-deoxyuridine Phosphoramidate Prodrugs," *J. Med. Chem.*, 2000, 43:4313-4318.

Morrison and Stone, "Mechanism of the Reaction Catalyzed by Dihydrofolate Reductase from *Escherichia coli*: pH and Deuterium Isotope Effects with NADPH as the Variable Substrate," *Biochem.*, 1988, 27:5499-5506.

Nakazawa et al., "UV and skin cancer: Specific p53 gene mutation in normal skin as a biologically relevant exposure measurement," *Proc. Natl. Acad. Sci. USA*, 1994, 91:360-364.

Ojida et al., "First Artificial Receptors and Chemosensors toward Phosphorylated Peptide in Aqueous Solution," *J. Am. Chem. Soc.*, 2002, 124:6256-6258.

Saboulard et al., "Characterization of the Activation Pathway of Phosphoramidate Triester Prodrugs of Stavudine and Zidovudine," *Molecular Pharmacology*, 1999, 56:693-704.

Sambrook et al. (eds)., *Molecular Cloning: A Laboratory Manual*, 1989, 2nd Ed., Cold Spring Harbor Laboratory Press, Cold Spring Harbor, NY; Sections 7.37-7.57, 9.47-9.57, 11.7-11.8, and 11.45-11.57.

Smith and Johnson, "Single-step purification of polypeptides expressed in *Escherichia coli* as fusions with glutathione S-transferase," *Gene*, 1988, 67:31-40.

Sticha et al., "Overexpression and Large-Scale Purification of Recombinant Hamster Polymorphic Arylamine *N*-Acetyltransferase as a Dihydrofolate Reductase Fusion Protein," *Protein Expr. Purif.*, 1997, 10:141-153

Stone and Morrison, "Kinetic Mechanism of the Reaction Catalyzed by Dihydrofolate Reductase from *Escherichia coli*," *Biochem.*, 1982, 21:3757-65.

Zhang et al., "A Continuous Spectrophotometric and Fluorimetric Assay for Protein Tyrosine Phosphatase Using Phosphotyrosine-Containing Peptides," *Anal. Biochem.*, 1993, 211:7-15.

* cited by examiner

```
atggcggaggaacaggtgaaccgcagcgccggcctggcccccgactgtgaggcctcggcgactgcagaaac
tacggtttcctcagtggggacctgtgaagccgctgccaagtcaccagagcccaaggactacgacagcacct
gcgtgttctgccggatcgcggggcggcaggacccgggcaccgaactcctgcactgcgagaatgaggaccta
atttgcttcaaagatatcaaaccagcagcaactcatcattatcttgtggtgccaaagaagcatattggaaa
ctgcagaactctaaggaaagatcaagtagaactggttgagaacatggtaactgttggaaaaaccattcttg
aaagaaataatttcactgacttcacgaatgtgaggatgggttttcatatgccaccattctgttccatttcc
cacttgcaccttcatgttctggcaccagtggatcagcttggcttcttatccaagttggtttatagagtcaa
ttcctattggtttatcacagctgatcacttgattgaaaaactaagaacatga (SEQ ID NO:1)

atggcggaggaacaggtgaaccgcagcgccggcctggcccccgactgtgaggcctcggcgactgcagaaac
tacggtttcctcagtggggacctgtgaagccgctggcaagtcaccagagcccaaggactacgacagcacct
gcgtgttctgccggatcgcggggcggcaggacccgggcaccgaactcctgcactgcgagaatgaggaccta
atttgcttcaaagatatcaaaccagcagcaactcatcattatcttgtggtgccaaagaagcatattggaaa
ctgcagaactctaaggaaagatcaagtagaactggttgagaacatggtaactgttggaaaaaccattcttg
aaagaaataatttcactgacttcacgaatgtgaggatgggttttcatatgccaccattctgttccatttcc
cacttgcaccttcatgttctggcaccagtggatcagcttggcttcttatccaagttggtttatagagtcaa
ttcctattggtttatcacagctgatcacttgattgaaaaactaagaacatga (SEQ ID NO:2)

gtggcagaagaaactatattcagcaaaattattcgtcgtgagatcccctccgatatcgtctaccaggatga
tctggtaacggcgtttcgcgatatttcgccgcaagcgccaacgcatattctgatcattccgaatatcctca
ttccgactgtgaacgacgtctcagctgagcatgagcaggcgctgggacgcatgatcaccgtagcggcaaaa
attgctgagcaagaaggtattgccgaagatggctatcgtctgatcatgaataccaaccgccatggcggaca
agaggtttaccacatccatatgcacttgttgggtggccgtccgctgggaccaatgctggcgcataaaggtc
tgtaa (SEQ ID NO:3)
```

Figure 3

```
MAEEQVNRSAGLAPDCEASATAETTVSSVGTCEAAAKSPEPKDYDSTCVFCRIAGRQDPGTELLHCENEDL
ICFKDIKPAATHHYLVVPKKHIGNCRTLRKDQVELVENMVTVGKTILERNNFTDFTNVRMGFHMPPFCSIS
HLHLHVLAPVDQLGFLSKLVYRVNSYWFITADHLIEKLRT  (SEQ ID NO:4)

MAEEQVNRSAGLAPDCEASATAETTVSSVGTCEAAGKSPEPKDYDSTCVFCRIAGRQDPGTELLHCENEDL
ICFKDIKPAATHHYLVVPKKHIGNCRTLRKDQVELVENMVTVGKTILERNNFTDFTNVRMGFHMPPFCSIS
HLHLHVLAPVDQLGFLSKLVYRVNSYWFITADHLIEKLRT  (SEQ ID NO:5)

MAEETIFSKIIRREIPSDIVYQDDLVTAFRDISPQAPTHILIIPNILIPTVNDVSAEHEQALGRMITVAAK
IAEQEGIAEDGYRLIMNTNRHGGQEVYHIHMHLLGGRPLGPMLAHKGL  (SEQ ID NO:6)
```

Figure 4

NUCLEOSIDE PHOSPHORAMIDATES AND NUCLEOSIDE PHOSPHORAMIDASES

CROSS REFERENCE TO RELATED APPLICATIONS

This application claims priority under 35 U.S.C. §119(e) of U.S. application Ser. No. 60/584,958, filed Jul. 2, 2004.

FEDERALLY SPONSORED RESEARCH OR DEVELOPMENT

The U.S. Government may have certain rights in this invention pursuant to Grant No. CA89615 awarded by the National Institute of Health.

TECHNICAL FIELD

This invention relates to nucleoside phosphoramidates, and more particularly to cleavage of nucleoside phosphoramidates by nucleoside phosphoramidases.

BACKGROUND

Nucleoside phosphoramidates have a demonstrated utility as pro-drugs of antiviral and anticancer nucleoside monophosphates. In general, there is a requirement that therapeutic nucleosides be converted to at least the corresponding monophosphate before demonstrating biological activity. Nevertheless, many nucleosides are not substrates for the requisite nucleoside kinase. To overcome this hurdle, several approaches have been investigated, including the delivery of nucleoside monophosphoramidates. Although, the nature of the enzyme responsible for phosphoramidate hydrolysis has not been determined, direct evidence of intracellular P—N bond hydrolysis has been demonstrated. Therefore, the identification and characterization of phosphoramidases may facilitate the design of tissue- and species-specific nucleoside phosphoramidates having therapeutic utility.

SUMMARY

In one aspect, the invention provides an isolated nucleic acid molecule. Nucleic acid molecules of the invention include a) a sequence shown in SEQ ID NO: 1, SEQ ID NO:2, or SEQ ID NO:3; b) a sequence having at least 85% sequence identity to SEQ ID NO: 1, SEQ ID NO:2, or SEQ ID NO:3; or c) a fragment of the sequence of a) or b). Generally, the nucleic acid molecule encodes a polypeptide having nucleoside phosphoramidase activity. The invention includes a purified polypeptide encoded by a nucleic acid molecule of the invention. Representative polypeptides include SEQ ID NO:4, SEQ ID NO:5, or SEQ ID NO:6. Vectors containing such nucleic acids are also provided by the invention.

In another aspect, the invention provides an article of manufacture (e.g., a kit). An article of manufacture of the invention can include a nucleoside phosphoramidate, a polypeptide having nucleoside phosphoramidase activity, and/or a nucleic acid molecule encoding a polypeptide having nucleoside phosphoramidase activity. An article of manufacture also can include instructions for using the kit.

In one embodiment, the nucleoside phosphoramidate is a purine phosphoramidate (e.g., a guanosine phosphoramidate). In some embodiments, the nucleic acid molecule encoding a polypeptide having nucleoside phosphoramidase activity comprises a) a sequence shown in SEQ ID NO:1, SEQ ID NO:2, or SEQ ID NO:3; b) a sequence having at least 85% sequence identity to SEQ ID NO: 1, SEQ ID NO:2, or SEQ ID NO:3; or c) a fragment of the sequence of a) or b). In certain embodiments, the polypeptide having nucleoside phosphoramidase activity has a sequence shown in SEQ ID NO:4, SEQ ID NO:5, or SEQ ID NO:6.

In another aspect, the invention provides methods of delivering a nucleoside phosphate compound to an individual in need of anti-viral or anti-cancer treatment. Such methods include providing a nucleoside phosphoramidate to the individual; and providing a polypeptide having nucleoside phosphoramidase activity or a nucleic acid molecule encoding a polypeptide having nucleoside phosphoramidase activity to the individual. For example, the nucleoside phosphate can be a nucleoside monophosphate, a nucleoside diphosphate, or a nucleoside triphosphate.

In some embodiments, the nucleoside phosphoramidate is a purine phosphoramidate (e.g., guanine phosphoramidate). In certain embodiments, the nucleoside phosphoramidase is encoded by a nucleic acid molecule having a sequence shown in SEQ ID NO:1, SEQ ID NO:2, or SEQ ID NO:3.

In still another aspect, the invention provides methods of screening nucleoside phosphoramidate compounds for cleavage by a nucleoside phosphoramidase enzyme. Such methods generally include contacting a nucleoside phosphoramidate test compound with a nucleoside phosphoramidase enzyme; and determining whether or not the nucleoside phosphoramidase enzyme cleaved the nucleoside phosphoramidate test compound. Alternatively, the invention provides for methods of screening nucleoside phosphoramidase enzymes for the ability to cleave a nucleoside phosphoramidate compound. Such methods generally include contacting a nucleoside phosphoramidase test enzyme with a nucleoside phosphoramidate, and determining whether or not the nucleoside phosphoramidase enzyme cleaved the nucleoside phosphoramidate test compound. In certain embodiments, the nucleoside phosphoramidase enzyme can be a chimeric enzyme.

In one embodiment, the nucleoside phosphoramidate test compound is a purine phosphoramidate (e.g., guanine phosphoramidate). In some embodiments, the nucleoside phosphoramidate test compound is a D enantiomer. In some embodiments, the determining step utilizes NMR spectroscopy or a fluorescent assay. As above, the nucleoside phosphoramidase can be encoded by a nucleic acid molecule having a sequence shown in SEQ ID NO:1, SEQ ID NO:2, or SEQ ID NO:3.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In addition, the materials, methods, and examples are illustrative only and not intended to be limiting. All publications, patent applications, patents, and other references mentioned herein are incorporated by reference in their entirety. In case of conflict, the present specification, including definitions, will control.

The details of one or more embodiments of the invention are set forth in the accompanying drawings and the description below. Other features, objects, and advantages of the invention will be apparent from the drawings and detailed description, and from the claims.

DESCRIPTION OF DRAWINGS

(FIG. 2A) AMP-NH$_2$ (5 mM) incubated with *E. coli* cell lysates (0.75 mg total protein) at 37° C. for 15 min; (FIG. 2B) for 30 min; (FIG. 2C) for 12 h. (FIG. 2D) Control: AMP-NH$_2$ (10 mM) incubated with pH 2.0 buffer at 37° C. for 12 h.

FIG. 3 is the nucleotide sequences encoding phosphoramidases from human (SEQ ID NOs: 1 and 2) and *E. coli* (SEQ ID NO:3).

FIG. 4 is the polypeptide sequences of phosphoramidases from human (SEQ ID NO:4 and 5) and *E. coli* (SEQ ID NO:6).

Like reference symbols in the various drawings indicate like elements.

DETAILED DESCRIPTION

Figure 1:
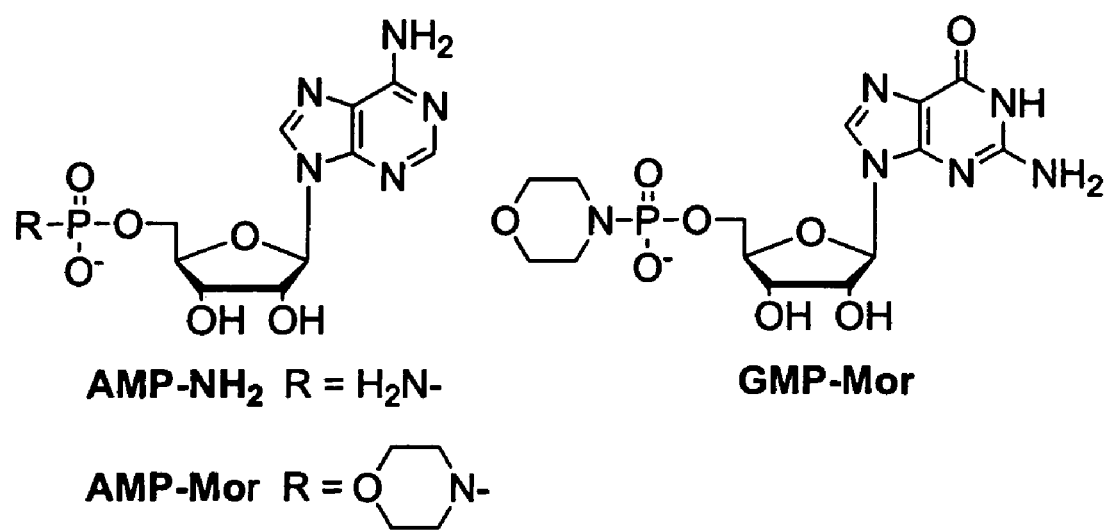
FIG. 1 shows structures of representative substrates.

The invention provides phosphoramidases from human and *E. coli* that exhibit broad specificity for both the nucleoside and the amine. These enzymes can be used to screen for potential therapeutic agents that are activated by phosphoramidate bond hydrolysis.

Nucleic Acids and Polypeptides

The invention provides for an isolated nucleic acid molecule that includes one of the sequences shown in SEQ ID NO:1, SEQ ID NO:2, or SEQ ID NO:3. The invention also provides for isolated nucleic acid molecules that have at least 85% sequence identity to SEQ ID NO: 1, SEQ ID NO:2, or SEQ ID NO:3. In addition, the invention provides for fragments of such nucleic acid molecules. Nucleic acid molecules of the invention generally encode polypeptides having nucleoside phosphoramidase activity. The amino acid sequences of representative polypeptides having nucleoside phosphoramidase activity include, without limitation, SEQ ID NO:4, SEQ ID NO:5, or SEQ ID NO:6.

As used herein, the term "nucleic acid molecule" can include DNA molecules and RNA molecules and analogs of the DNA or RNA molecule generated using nucleotide analogs. A nucleic acid molecule of the invention can be single-stranded or double-stranded, and the strandedness will depend upon its intended use. The invention further encompasses nucleic acid molecules that differ in nucleotide sequence. Nucleic acid molecules that differ in sequence from the original nucleic acid sequence can be generated by standard techniques, such as site-directed mutagenesis or PCR-mediated mutagenesis. In addition, nucleotide changes can be introduced randomly along all or part of a nucleic acid molecule such as by saturation mutagenesis. Alternatively, nucleotide changes can be introduced into a sequence by chemically synthesizing a nucleic acid molecule having such changes.

To calculate percent sequence identity, two sequences are aligned and the number of identical matches of nucleotides or amino acid residues between the two sequences is determined. The number of identical matches is divided by the length of the aligned region (i.e., the number of aligned nucleotides or amino acid residues) and multiplied by 100 to arrive at a percent sequence identity value. It will be appreciated that the length of the aligned region can be a portion of one or both sequences up to the full-length size of the shortest sequence. It will be appreciated that a single sequence can align differently with other sequences and hence, can have different percent sequence identity values over each aligned region. It is noted that the percent identity value is usually rounded to the nearest integer. For example, 78.1%, 78.2%, 78.3%, and 78.4% are rounded down to 78%, while 78.5%, 78.6%, 78.7%, 78.8%, and 78.9% are rounded up to 79%. It is also noted that the length of the aligned region is always an integer.

The alignment of two or more sequences to determine percent sequence identity is performed using the algorithm described by Altschul et al. (1997, *Nucleic Acids Res.*, 25:3389–3402) as incorporated into BLAST (basic local alignment search tool) programs, available at ncbi.nlm.nih.gov on the World Wide Web. BLAST searches can be performed to determine percent sequence identity between a nucleic acid molecule of the invention and any other sequence or portion thereof aligned using the Altschul et al. algorithm. BLASTN is the program used to align and compare the identity between nucleic acid sequences, while BLASTP is the program used to align and compare the identity between amino acid sequences. When utilizing BLAST programs to calculate the percent identity between a sequence of the invention and another sequence, the default parameters of the respective programs are used. Sequence analysis of nucleic acid sequences can be performed used BLAST version 2.2.9 (updated on May 12, 2004).

As used herein, an "isolated" nucleic acid molecule is a nucleic acid molecule that is separated from other nucleic acid molecules that are usually associated with the isolated nucleic acid molecule. Thus, an "isolated" nucleic acid molecule includes, without limitation, a nucleic acid molecule that is free of sequences that naturally flank one or both ends of the nucleic acid in the genome of the organism from which the isolated nucleic acid is derived (e.g., a cDNA or genomic DNA fragment produced by PCR or restriction endonuclease digestion). Such an isolated nucleic acid molecule is generally introduced into a vector (e.g., a cloning vector, or an expression vector) for convenience of manipulation or to generate a fusion nucleic acid molecule. In addition, an isolated nucleic acid molecule can include an engineered nucleic acid molecule such as a recombinant or a synthetic nucleic acid molecule. A nucleic acid molecule existing among hundreds to millions of other nucleic acid molecules within, for example, a nucleic acid library (e.g., a cDNA, or genomic library) or a portion of a gel (e.g., agarose, or polyacrylamine) containing restriction-digested genomic DNA is not to be considered an isolated nucleic acid.

Isolated nucleic acid molecules of the invention can be obtained using techniques routine in the art. For example, isolated nucleic acids within the scope of the invention can be obtained using any method including, without limitation, recombinant nucleic acid technology, and/or the polymerase chain reaction (PCR). General PCR techniques are described, for example in *PCR Primer: A Laboratory Manual*, Dieffenbach & Dveksler, Eds., Cold Spring Harbor Laboratory Press, 1995. Recombinant nucleic acid techniques include, for example, restriction enzyme digestion and ligation, which can be used to isolate a nucleic acid molecule of the invention. Isolated nucleic acids of the invention also can be chemically synthesized, either as a single nucleic acid molecule or as a series of oligonucleotides. In addition, isolated nucleic acid molecules of the invention also can be obtained by mutagenesis using common molecular cloning techniques (e.g., site-directed mutagenesis). Possible mutations include, without limitation, deletions, insertions, substitutions, and combinations thereof.

Vectors containing nucleic acid molecules also are provided by the invention. Vectors, including expression vectors, suitable for use in the present invention are commercially available and/or produced by recombinant DNA technology methods routine in the art. A vector containing a nucleic acid molecule can have elements necessary for expression operably linked to such a nucleic acid, and further can include sequences such as those encoding a selectable marker (e.g., a sequence encoding antibiotic resistance), and/or those that can be used in purification of a polypeptide (e.g., a His tag).

Elements necessary for expression include nucleic acid sequences that direct and regulate expression of nucleic acid coding sequences. One example of an element necessary for expression is a promoter sequence. Elements necessary for expression also can include ribosome-binding sites, introns, enhancer sequences, response elements, or inducible elements that modulate expression of a nucleic acid. Elements necessary for expression can be of bacterial, yeast, insect, mammalian, or viral origin and vectors can contain a combination of elements from different origins. Elements necessary for expression are described, for example, in Goeddel, 1990, *Gene Expression Technology: Methods in Enzymology*, 185, Academic Press, San Diego, Calif. As used herein, operably linked means that a promoter and/or other regulatory element(s) are positioned in a vector relative to a nucleic acid in such a way as to direct or regulate expression of the nucleic acid.

Another aspect of the invention pertains to host cells into which a vector of the invention, e.g., an expression vector, or an isolated nucleic acid molecule of the invention has been introduced. The term "host cell" refers not only to the particular cell but also to the progeny or potential progeny of such a cell. A host cell can be any prokaryotic or eukaryotic cell. For example, host cells can include bacterial cells such as *E. coli*, insect cells, yeast cells, or mammalian cells (such as Chinese hamster ovary cells (CHO) or COS cells). Other suitable host cells are known to those skilled in the art. Many methods for introducing nucleic acids into host cells, both in vivo and in vitro, are well known to those skilled in the art and include, without limitation, calcium phosphate precipitation, electroporation, heat shock, lipofection, microinjection, and viral-mediated nucleic acid transfer.

One aspect of the invention pertains to purified polypeptides, as well as polypeptide fragments. A "polypeptide" refers to a polypeptide encoded by a nucleic acid molecule. The term "purified" polypeptide as used herein refers to a polypeptide that has been separated or purified from cellular components that naturally accompany it. Typically, the polypeptide is considered "purified" when it is at least 70% (e.g., at least 75%, 80%, 85%, 90%, 95%, or 99%) by dry weight, free from the proteins and naturally occurring molecules with which it is naturally associated. Since a polypeptide that is chemically synthesized is, by nature, separated from the components that naturally accompany it, a synthetic polypeptide is "purified."

Polypeptides can be purified from natural sources (e.g., a biological sample) by known methods such as DEAE ion exchange, gel filtration, and hydroxyapatite chromatography. A purified polypeptide also can be obtained by expressing a nucleic acid in an expression vector, for example. In addition, a purified polypeptide can be obtained by chemical synthesis. The extent of purity of a polypeptide can be measured using any appropriate method, e.g., column chromatography, polyacrylamide gel electrophoresis, or HPLC analysis.

In addition to naturally-occurring polypeptides, the skilled artisan will further appreciate that changes can be introduced into a nucleic acid molecule as discussed herein, thereby leading to changes in the amino acid sequence of the encoded polypeptide. For example, changes can be introduced into a nucleic acid coding sequence leading to conservative and/or non-conservative amino acid substitutions at one or more amino acid residues. A "conservative amino acid substitution" is one in which one amino acid residue is replaced with a different amino acid residue having a similar side chain. Similarity between amino acid residues has been assessed in the art. For example, Dayhoff et al. (1978, in *Atlas of Protein Sequence and Structure*, Vol. 5, Suppl. 3, pp 345–352) provides frequency tables for amino acid substitutions that can be employed as a measure of amino acid similarity. A non-conservative substitution is one in which an amino acid residue is replaced with an amino acid residue that does not have a similar side chain.

The invention also provides for chimeric or fusion polypeptides. As used herein, a "chimeric" or "fusion" polypeptide includes one polypeptide operatively linked to a heterologous polypeptide. The heterologous polypeptide can be at either the N-terminus or C-terminus of the polypeptide. Within a chimeric or fusion polypeptide, the term "operatively linked" is intended to indicate that the two polypeptides are encoded in-frame relative to one another. In a fusion polypeptide, the heterologous polypeptide generally has a desired property such as the ability to purify the fusion polypeptide (e.g., by affinity purification). A chimeric or fusion polypeptide of the invention can be produced by standard recombinant DNA techniques, and can use commercially available vectors.

Polypeptides often contain multiple domains (e.g., structural, functional), which can be shuffled, swapped, or recombined to gain new and/or different function. For example, nucleic acid molecules (e.g., SEQ ID NOs: 1, 2, or 3) can be manipulated using standard techniques to delete or inactivate activity encoding regions, insert or exchange regions from different molecules encoding corresponding activities from the same or different biosynthesis systems, or be otherwise mutated using standard procedures for obtaining genetic alterations. Mutations can be made to the native sequences using conventional techniques such as those described above. For example, a domain having a particular activity from one enzyme can be exchanged or replaced with a domain having a corresponding activity from, for example, a homologous or non-homologous enzyme. Alternatively, a domain having a particular activity from one enzyme can be exchanged or replaced with a domain having an unrelated activity from the same or a different enzyme.

If replacement of a particular nucleic acid region encoding a domain is to be made, this replacement can be conducted in vitro using suitable restriction enzymes and cloning techniques or can be effected in vivo using recombinant techniques involving homologous sequences framing the replacement region in a donor plasmid and a receptor region in a recipient plasmid. A representative exchange system that involves plasmids that have different temperature sensitivities is described in PCT Publication No. WO 96/40968.

A polypeptide commonly used in a fusion polypeptide for purification is glutathione S-transferase (GST), although numerous other polypeptides are available and can be used. In addition, a proteolytic cleavage site can be introduced at the junction between a polypeptide and a heterologous polypeptide to enable separation of the two polypeptides subsequent to purification of the fusion polypeptide. Enzymes that cleave such proteolytic sites include Factor Xa, thrombin, or enterokinase. Representative expression vectors encoding a heterologous polypeptide that can be used in affinity purification of a polypeptide include pGEX (Pharmacia Biotech Inc; Smith & Johnson, 1988, *Gene*, 67:31–40), pMAL (New England Biolabs, Beverly, Mass.) and pRIT5 (Pharmacia, Piscataway, N.J.).

Nucleic acid molecules and polypeptides can be detected using a number of different methods. Methods for detecting nucleic acids include, for example, PCR and nucleic acid hybridizations (e.g., Southern blot, Northern blot, or in situ hybridizations). Specifically, oligonucleotides (e.g., oligonucleotide primers) capable of amplifying a target nucleic acid can be used in a PCR reaction. PCR methods generally include the steps of obtaining a sample, isolating nucleic acid (e.g., DNA, RNA, or both) from the sample, and contacting the nucleic acid with one or more oligonucleotide primers that hybridize(s) with specificity to the template nucleic acid under conditions such that amplification of the template nucleic acid occurs. In the presence of a template nucleic acid, an amplification product is produced. Conditions for amplification of a nucleic acid and detection of an amplification product are known to those of skill in the art (see, e.g., *PCR Primer: A Laboratory Manual*, 1995, Dieffenbach & Dveksler, Eds., Cold Spring Harbor Laboratory Press, Cold Spring Harbor, N.Y.; and U.S. Pat. Nos. 4,683, 195; 4,683,202; 4,800,159; and 4,965,188). Modifications to the original PCR also have been developed. For example, anchor PCR, RACE PCR, RT-PCR, or ligation chain reaction (LCR) are additional PCR methods known in the art (see, e.g., Landegran et al., 1988, *Science*, 241:1077–1080; and Nakazawa et al., 1994, *Proc. Natl. Acad. Sci. USA*, 91:360–364).

As used herein, "standard amplification conditions" refer to the basic components of an amplification reaction mix, and cycling conditions that include multiple cycles of denaturing the template nucleic acid, annealing the oligonucleotide primers to the template nucleic acid, and extension of the primers by the polymerase to produce an amplification product (see, for example, U.S. Pat. Nos. 4,683,195; 4,683, 202; 4,800,159; and 4,965,188). The basic components of an amplification reaction mix generally include, for example, about 10–25 nmole of each of the four deoxynucleoside triphosphates, (e.g., dATP, dCTP, dTTP, and dGTP, or analogs thereof), 10–100 pmol of each primer, template nucleic acid, and a polymerase enzyme. The reaction components are generally suspended in a buffered aqueous solution having a pH of between about 7 and about 9. The aqueous buffer can further include one or more co-factors (e.g., $Mg^{2+}$, $K^+$) required by the polymerase. Additional components such as DMSO are optional. Template nucleic acid is typically denatured at a temperature of at least about 90° C., and extension from primers is typically performed at a temperature of at least about 72° C.

The annealing temperature can be used to control the specificity of amplification. The temperature at which primers anneal to template nucleic acid must be below the Tm of each of the primers, but high enough to avoid non-specific annealing of primers to the template nucleic acid. The Tm is the temperature at which half of the DNA duplexes have separated into single strands, and can be predicted for an oligonucleotide primer using the formula provided in section 11.46 of Sambrook et al. (1989, *Molecular Cloning: A Laboratory Manual*, 2nd Ed., Cold Spring Harbor Laboratory Press, Cold Spring Harbor, N.Y.). Non-specific amplification products are detected as bands on a gel that are not the size expected for the correct amplification product. It can be appreciated by those of skill in the art that appropriate positive and negative controls should be performed with every set of amplification reactions to avoid uncertainties related to contamination and/or non-specific annealing of oligonucleotide primers and extension therefrom.

A pair of primers in an amplification reaction must anneal to opposite strands of the template nucleic acid, and should be an appropriate distance from one another such that the polymerase can effectively polymerize across the region and such that the amplification product can be readily detected using, for example, electrophoresis. Oligonucleotide primers can be designed using, for example, a computer program such as OLIGO (Molecular Biology Insights Inc., Cascade, Co.) to assist in designing primers that have similar melting temperatures. Typically, oligonucleotide primers are 10 to 30 or 40 or 50 nucleotides in length (e.g. 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides in length), but can be longer or shorter if appropriate amplification conditions are used. Oligonucleotides of the invention can be obtained by restriction enzyme digestion of a nucleic acid molecule or can be prepared by standard chemical synthesis and other known techniques.

Alternatively, a nucleic acid can be detected using a labeled oligonucleotide probe capable of hybridizing to nucleic acids on a Southern blot. In the presence of homologous nucleic acid, a hybridization complex is produced between the nucleic acid and the oligonucleotide probe. Hybridization between nucleic acid molecules is discussed in detail in Sambrook et al. (1989, *Molecular Cloning: A Laboratory Manual*, $2^{nd}$ Ed., Cold Spring Harbor Laboratory Press, Cold Spring Harbor, N.Y.; Sections 7.37–7.57, 9.47–9.57, 11.7–11.8, and 11.45–11.57).

For oligonucleotide probes less than about 100 nucleotides, Sambrook et al. discloses suitable Southern blot conditions in Sections 11.45–11.46. The Tm between a sequence that is less than 100 nucleotides in length and a second sequence can be calculated using the formula provided in Section 11.46. Sambrook et al. additionally discloses prehybridization and hybridization conditions for a Southern blot that uses oligonucleotide probes greater than about 100 nucleotides (see Sections 9.47–9.52). Hybridizations with an oligonucleotide greater than 100 nucleotides generally are performed 15–25° C. below the Tm. The Tm between a sequence greater than 100 nucleotides in length and a second sequence can be calculated using the formula provided in Sections 9.50–9.51 of Sambrook et al. Additionally, Sambrook et al. recommends the conditions indicated in Section 9.54 for washing a Southern blot that has been probed with an oligonucleotide greater than about 100 nucleotides.

The conditions under which membranes containing nucleic acids are prehybridized and hybridized, as well as the conditions under which membranes containing nucleic acids are washed to remove excess and non-specifically bound probe can play a significant role in the stringency of the hybridization. Such hybridizations can be performed, where appropriate, under moderate or high stringency conditions. Such conditions are described, for example, in Sambrook et al. section 11.45–11.46. For example, washing conditions can be made more stringent by decreasing the salt concentration in the wash solutions and/or by increasing the temperature at which the washes are performed. In addition, interpreting the amount of hybridization can be affected, for example, by the specific activity of the labeled oligonucleotide probe, by the number of probe-binding sites on the template nucleic acid to which the probe has hybridized, and by the amount of exposure of an autoradiograph or other detection medium.

It will be readily appreciated by those of ordinary skill in the art that although any number of hybridization and washing conditions can be used to examine hybridization of a probe nucleic acid molecule to immobilized target nucleic acids, it is more important to examine hybridization of a probe to target nucleic acids under identical hybridization, washing, and exposure conditions. Preferably, the target nucleic acids are on the same membrane.

A nucleic acid molecule is deemed to hybridize to a target nucleic acid but not to a non-homologous nucleic acid if hybridization to the homologous target nucleic acid is at least 5-fold (e.g., at least 6-fold, 7-fold, 8-fold, 9-fold, 10-fold, 20-fold, 50-fold, or 100-fold) greater than hybridization to the non-homologous nucleic acid. The amount of hybridization can be quantitated directly on a membrane or from an autoradiograph using, for example, a PhosphorImager or a Densitometer (Molecular Dynamics, Sunnyvale, Calif.).

Detection of an amplification product or a hybridization complex is usually accomplished using detectable labels. The term "label" with regard to a nucleic acid is intended to encompass direct labeling of a nucleic acid by coupling (i.e., physically linking) a detectable substance to the nucleic acid, as well as indirect labeling of the nucleic acid by reactivity with another reagent that is directly labeled with a detectable substance. Detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^3H$. An example of indirect labeling includes end-labeling a nucleic acid with biotin such that it can be detected with fluorescently labeled streptavidin.

Methods of Screening

The invention provides for methods of screening nucleoside phosphoramidate compounds for cleavage by a nucleoside phosphoramidase enzyme. For example, various nucleoside phosphoramidate test compounds can be exposed to tissue-specific or cell-specific nucleoside phosphoramidases or a tissue-specific or cell-specific lysate. The compound can be monitored to determine whether or not cleavage occurred. Using these methods, particular phosphoramidate compounds can be identified that are cleaved in a tissue-specific or cell-specific manner. The invention also provides for methods of screening nucleoside phosphoramidase enzymes (wild type of chimeric) for the ability to cleave a particular nucleoside phosphoramidate compound.

Nucleoside phosphoramidases (EC 3.9.1) are considered hydrolases, and typically hydrolyze nucleoside 5'-monophosphoramidates into nucleoside 5'-phosphates and ammonia. As discussed above, nucleoside phosphoramidases useful in the invention can be encoded by the nucleic acid molecules shown in SEQ ID NO:1, SEQ ID NO:2, or SEQ ID NO:3 (e.g., SEQ ID NO:4, 5, or 6). Also as discussed above, nucleoside phosphoramidases useful in the invention can be chimeric enzymes in which structural or functional domains have been replaced or exchanged between any of SEQ ID NO:4, 5, or 6, or another nucleoside phosphoramidase that exhibits useful activity (e.g., substrate recognition, or enzymatic cleavage). Other nucleoside phosphoramidases can be found, for example, in GenBank (see, for example, GenBank Accession Nos. BC070415, BC007090, and NM 138571).

Generally, as used herein, nucleoside phosphoramidates refer to nucleoside monophosphates having an amine group. Phosphoramidates useful in the invention can be purine phosphoramidates (e.g., guanine phosphoramidate, adenosine phosphoramidate), or alternatively, pyrimidine phosphoramidates (cytosine phosphoramidate, or thymidine phosphoramidate). For example, U.S. Pat. No. 6,475,985 discloses a number of phosphoramidate compounds that can be used in this invention.

Methods for detecting cleavage of a phosphoramidate compound are known in the art. For example, NMR spectroscopy as described herein can be used. Fluorescent labels in conjunction with spectroscopy, fluorometry, or analytical flow cytometry also can be used to detect cleavage of the phosphoramidate. See, for example, *J. Am. Chem. Soc.*, 2002, 124:6256–8; and *Anal. Biochem.*, 1993, 211:7–15. Liquid chromatography mass spectrometry is another method that can be used to detect cleavage of the phosphoramidate (see, for example, U.S. Pat. No. 6,396,057). Fluorescent assays and mass spectrometry assays are well known methods in the art.

Methods of Delivery

The invention provides for methods of delivering a nucleoside phosphate compound to an individual in need of anti-viral, anti-cancer, and anti-bacterial treatment. Such methods can include providing a nucleoside phosphoramidate to the individual, such as a nucleoside phosphoramidate compound identified in a screening method of the invention. A polypeptide having nucleoside phosphoramidase activity or a nucleic acid molecule encoding a polypeptide having nucleoside phosphoramidase activity to the individual can also be delivered to an individual. Such a nucleoside phosphoramidase can be a wild type enzyme, or can be a chimeric enzyme that has been customized or designed for cleavage of a particular nucleoside phosphoramidate.

A nucleoside phosphoramidate, a polypeptide having nucleoside phosphoramidase activity, or a combination of both can be provided to an individual in a pharmaceutically acceptable carrier using a number of routes of administration such as orally, nasally, intravenously, intraperitoneally, intramuscularly, subcutaneously, intrathecally, intradermally, intracisternally or intraventricularly. As used herein, "pharmaceutically acceptable carrier" is intended to include any and all solvents, dispersion media, coatings, antibacterial and anti-fungal agents, isotonic and absorption delaying agents, and the like, compatible with pharmaceutical administration. The use of such media and agents for pharmaceutically active substances is well known in the art.

A pharmaceutical composition of the invention is formulated to be compatible with its intended route of administration. Solutions or suspensions can include the following components: a sterile diluent such as water for injection, saline solution (e.g., phosphate buffered saline (PBS)), fixed oils, a polyol (for example, glycerol, propylene glycol, and liquid polyetheylene glycol, and the like), glycerine, or other synthetic solvents; antibacterial and antifungal agents such as parabens, chlorobutanol, phenol, ascorbic acid, thimerosal, and the like; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol or sorbitol, and sodium chloride in the composition. Prolonged administration of the injectable compositions can be brought about by including an agent that delays absorption. Such agents include, for example, aluminum monostearate and gelatin.

Oral compositions generally include an inert diluent or an edible carrier. Oral compositions can be liquid, or can be enclosed in gelatin capsules or compressed into tablets. Pharmaceutically compatible binding agents, and/or adjuvant materials can be included as part of an oral composition. Tablets, pills, capsules, troches and the like can contain any of the following ingredients, or compounds of a similar nature: a binder such as microcrystalline cellulose, gum tragacanth or gelatin; an excipient such as starch or lactose; a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. For transdermal or topical administration, the active compounds can be formulated into ointments, salves, gels, or creams as generally known in the art.

It is especially advantageous to formulate compositions in dosage unit form for ease of administration and uniformity of dosage. Dosage unit form as used herein refers to physically discrete units suited as unitary dosages for an individual to be treated; each unit containing a predetermined quantity of active compound calculated to produce the desired therapeutic effect in association with the required pharmaceutical carrier. The dosage unit forms of the invention are dependent upon the amount of a compound necessary to treat the individual. The amount of a compound necessary can be formulated in a single dose, or can be formulated in multiple dosage units. Treatment of an individual may require a one-time dose, or may require repeated doses.

Vectors for administering nucleic acids that encode biologically useful proteins (e.g., a polypeptide having nucleoside phosphoramidase activity) to an individual are known in the art. Current virus-based nucleic acid delivery vectors are typically derived from animal viruses, such as adenovirus, adeno-associated virus, retroviruses, lentiviruses, vaccinia virus, herpes viruses and bovine papilloma virus. Vectors for nucleic acid delivery usually have been genetically modified such that the native tropism and pathogenicity of the virus have been altered or removed. The genome of a virus also can be modified to increase its infectivity and to accommodate packaging of nucleic acids encoding, for example, a biologically useful protein. In addition, non-viral vectors and methods of using such vectors for nucleic acid delivery are known to those of skill in the art. The following descriptions are representative examples only.

Retroviruses typically mediate high nucleic acid transfer efficiency and expression. Retroviruses have an RNA genome that replicates through a DNA intermediate. Retroviruses enter a cell by direct fusion to the plasma membrane and integrate into the host chromosome during cell division. Lentiviruses are a genus of retroviruses that includes human immunodeficiency virus (HIV). Lentiviruses, unlike other retroviruses, are able to infect non-dividing cells and have been shown to infect and express nucleic acid in neuronal cells.

Adenoviruses contain a linear double-stranded DNA genome that can be engineered to inactivate its ability to replicate in the normal lytic life cycle. Adenoviruses enter a cell by receptor-mediated endocytosis and do not integrate into the genome of a host organism. Adenoviruses, therefore, are able to infect dividing or non-dividing cells. The native tropism of adenovirus is for a receptor naturally found on epithelial cells. Adenoviral vectors have been introduced and efficiently expressed in the cerebrospinal fluid of dogs and in the brain of rats, indicating successful adenoviral-mediated gene transfer to cerebral circulation.

Adeno-associated viruses have a single-stranded DNA genome, and demonstrate a broad range of tropism and infectivity, although they exhibit no human pathogenicity. Adeno-associated viruses exhibit site-specific integration and can infect non-dividing cells. Muscle cells and neurons have been the most efficient targets for nucleic acid delivery by adeno-associated viruses, and receptors and co-receptors for adeno-associated viruses have been identified.

The ability of herpes simplex virus type 1 (HSV-1) to establish a lifelong latent infection within neurons has led to interest in the use of herpes viruses as neuronal gene delivery vectors. HSV-1 contains a DNA genome and can package large amounts of foreign DNA (up to about 30–40 kb). In addition, use of the HSV latency-associated promoter allows high levels of expression of nucleic acids during periods of viral latency.

Viral vectors for in vivo expression of nucleic acids can be administered to an individual via numerous routes as described above. Administration of a genetically engineered virus to an individual and optimal expression of a nucleic acid encoding a polypeptide is more effective with any or all of the following: a sufficient level of expression of the nucleic acid; little or no expression of viral genes; minimal viral nucleic acid replication; no viral replication; minimal recombination between viruses (e.g., between genetically engineered viruses or between a genetically engineered virus and a non-genetically engineered virus); and minimal complementation of mutated or absent viral genes (e.g., a replication-deficient virus). In addition, it is desirable to avoid or eliminate any immune response in the individual (e.g., production of neutralizing antibodies) directed towards the virus.

Article of Manufacture

The invention also provides for an article of manufacture (e.g., a kit). An article of manufacture can include components such as a nucleoside phosphoramidate, a polypeptide having nucleoside phosphoramidase activity, and/or a nucleic acid molecule encoding a polypeptide having nucleoside phosphoramidase activity. Such components can be formulated for administration as described above, and can be, for example, enclosed in tablets, elixirs, ampoules, disposable syringes or multiple dose vials made of glass or plastic. An article of manufacture of the invention also can include instructions for administering either or both the nucleoside phosphoramidate and the nucleoside phosphoramidase to an individual.

The invention will be further described in the following examples, which do not limit the scope of the invention described in the claims.

EXAMPLES

Example 1

Cloning and Characterizing a Phosphoramidase

The enzyme responsible for hydrolysis of AZT amino acid phosphoramidates was cloned and characterized. After construction of a cDNA library from peripheral blood mononuclear cells (PBMCs) in T7Select10-3b phage, the phage display technique was employed to isolate the enzyme by affinity chromatography. After three rounds of phage selection and ampilification with an affinity column constructed from the L-tryptophan carbamate, DNA from ten selected plaques was amplified by PCR and sequenced. While six of the selected clones proved to be non-coding sequences, four of the clones were identified as human histidine triad nucleotide-binding protein 1(Hint1). Hint1 is a member of the HIT protein superfamily, which consists of a recently identified adenosine 5'-monophosphoramide hydrolases from rabbit and yeast. Amplification of the sequence for human Hint1 occurred, suggesting that the human homologue is able to bind to the affinity column. Human Hint1 was over-expressed, purified, and shown to efficiently hydrolyze adenosine phosphoramidate and to a lesser extent, AZT tryptophan phosphoramidate.

In addition, E. coli possesses a homologue of hHINT1, designated ycfF. The putative bacterial phosphoramidase was cloned and over-expressed as described for the human homologue, and found to be a nucleoside phosphoramidase.

Table 1 shows the catalytic activity of the enzymes. Velocity of the enzymes was determined at pH 7.2 at room temperature in the presence of 10 mM AMPNH$_2$.

TABLE 1

Catalytic activities

| Enzyme | Velocity (nmol/µg/min) |
|---|---|
| hHINT1 | 5.46 |
| ycfF | 14.19 |
| Rabbit HINT1 | 1.71[b] |
| Yeast HNT | 7.57[b] |

[b]Bieganowski et al, 2002, J. Biol. Chem., 277: 10852–60

Example 2

Evaluation of Phosphoramidase Activity in E. coli Cell Lysates

Adenosine 5'-monophosphoramidate (AMP-NH$_2$) was used to investigate the phosphoramidase activity in E. coli cell lysates since it has been shown to be a specific substrate for rabbit and yeast Hint hydrolases. Phosphoramidase activity in cell lysates was measured by the $^1$H-decoupling mode of phosphorus-31 NMR spectroscopy (Varian VAC-300 spectrometer), which can clearly distinguish the substrate, AMP-NH$_2$, and the product, adenosine 5'-monophosphate (AMP). NMR spectrometry is suitable for quantitation by integration of the area under the peak, which is proportional to the amount of nuclei present. The relative ratio of peak areas can be used to calculate the amount of turnover corrected based on a standard curve.

Cell lysates from E. coli Tuner(DE3)pLacI cells (Novagen) were obtained by treatment with lysozyme (1 mg/ml) and the DNA was precipitated by protamine sulfate followed by centrifugation to remove cell debris. The supernatant was dialyzed extensively against Buffer A (20 mM Tris (pH 7.0); 1 mM EDTA; 1 mM DTT, 0.01 mM PMSF) to remove cellular phosphates and nucleotides. Phosphate free cell lysates (0.75 mg total protein) were incubated with 5 mM AMP-NH$_2$ in 0.5 ml reaction buffer (0.5 mM MgCl$_2$, 20 mM HEPES (pH 7.2)) at 37° C. for intervals of 15 min, 30 min, and 12 h. The reactions were terminated by snap freezing in a dry ice/acetone slush bath and lyophilized for 5 h. The samples were then dissolved in NMR buffer (600 µL, 50 mM EDTA, 20 mM HEPES (pH 7.2), and 1 mM TMP (trimethylphosphate, internal standard)) and the insoluble portion was spun down by centrifugation at 12,500×g for 5 min. A $^{31}$P NMR spectrum was then collected for the supernatant. For the low pH control experiment, 10 mM AMP-NH$_2$ in reaction buffer (500 µL, pH 2.0) was incubated at 37° C. for 12 h and the $^{31}$P signal was detected under the same conditions.

Example 3

Genetic Deletion of E. coli hinT

The E. coli hinT gene in strain BW25113 was disrupted as previously described (Datsenko & Wanner, 2000, PNAS USA, 97:6640–6645). Plasmid pKD3 and primers 7024 and 7025 (Table 2) were used for amplification of the chloramphenicol resistance marker (Cm$^r$). Stable chloramphenicol resistant transformants of BW25113 were tested by PCR with primers 7026 and 7027 to confirm correct recombination of the Cm$^r$ marker into the hinT locus. A strain that tested positive by PCR was named BB1. Strain BB3 was constructed by removing the antibiotic resistance marker using Red recombinase as described previously (Datsenko & Wanner, supra). The hinT gene was amplified from the chromosomal DNA of E. coli strain BW25113 with primers 7328 and 7329. The product of this reaction was cloned into Bluescript SK+ using EcoRI and BamHI sites included in the primers' sequences. The resulting plasmid was named pB429. Mutagenesis of phagemid DNA was performed as described (Kunkel et al., 1987, Methods Enzymol., 154: 367–82) with primer 7330 resulted in plasmid pB431 containing hinT with an H101A substitution. Plasmids pB432 and pB433 were obtained by cloning HindIII-EcoRI fragments containing wild type and H101A mutated alleles of hinT from plasmids pB429 and pB431 into plasmid pACYC184. All E. coli transformations were performed by electroporation.

TABLE 2

Summary of the specific activity (nmol nmol$^{-1}$ min$^{-1}$) of the recombinant purified Hint hydrolases

| Substrate* | E. coli hinT-DHFR | Human Hint1-DHFR | E. coli hinT | Human Hint1 | Rabbit Hint1 |
|---|---|---|---|---|---|
| AMP-NH$_2$ | 753 ± 2 | 388 ± 45 | 526 ± 27 | 196 ± 33 | 70.0 ± 1.3 |
| AMP-Mor | 411 ± 4 | 43.4 ± 4.0 | 360 ± 1 | 45.0 ± 0 | 26.6 ± 0.6 |
| GMP-Mor | 675 ± 17 | 87.2 ± 11.8 | 669 ± 1 | 78.7 ± 1.3 | 48.6 ± 0.4 |

Example 4

Plasmid Constructions

The expression construct pPH70D in which the *E. coli* DHFR (dihydrofolate reductase) gene followed by a thrombin cleavage site were incorporated in the expression vector was described previously (Sticha et al., 1997, *Protein Expr. Purif.*, 10:141–153). The N-terminus of desired proteins were fused to DHFR with a 15 amino acid thrombin linker originally described in Sticha et al. (supra). The fusion proteins can be first purified using methotrexate (MTX) affinity chromatography followed by cleavage with human thrombin to release the native proteins. Both plasmids were constructed by replacing the hamster polymorphic N-acetyltransferase 2 (NAT2) in pPH70D with the desired proteins.

To create plasmid pTFCF15DmY, *E. coli* genomic DNA was purified from K12 strain EMG2 (ATCC) as previously described (Current protocols in Molecular Biology, Supplement 56, 2.4). Using isolated genomic DNA as the template, a 385 bp fragment was amplified by PCR with primers 101 and 102, which contain the restriction sites XhoI and XbaI, respectively. The PCR product was ligated into the T/A cloning vector, pSTBlue 1 (Novagen). Novablue supercompetent cells were transformed with the ligation mixture, and insert-containing clones were selected by blue/white screening on X-gal/IPTG indicator plates. The resulting plasmid pTFCY-TA was digested with XhoI and XbaI and subcloned into digested and purified pPH70D. The ligation mixture was transformed into chemically competent *E. coli* DH5α cells (Novagen). The plasmid pTFCF15DmY was purified with QIAprep Spin Miniprep kit (Qiagen) and the desired sequence was confirmed by DNA sequencing (Advanced Genetic Analysis Center, University of Minnesota). The over-expression *E. coli* strain Tuner(DE3)pLacI cells (Novagen) were made competent (Hanahan, 1983, *J. Mol. Biol.*, 166:557–580) and transformed with pTFCF15DmY.

To express human Hint1, the pJLCF15DmH plasmid was created following a similar procedure described above. Total mRNA was isolated using Straight A's mRNA isolation System (Novagen) from CEM cell line, a human T-lymphoblast leukemia cell line, and the cDNA library was synthesized by reverse transcriptase and DNA polymerase I/RNase H according to the manufacturer's protocol (Novagen). Using this cDNA library as template, the human HINT1 cDNA was amplified by PCR with primers 103 and 104.

Example 5

Expression and Purification of Recombinant Proteins

The cell growth and cell lysates extraction were described previously (Sticha et al., supra) except that 0.5 mM IPTG was used for induction. Bacterial or human Hint-DHFR fusion proteins were purified by methotrexate (MTX)-agarose (Sigma) using a 12.5-ml column, washed with 40 column volumes of wash buffer A (20 mM Tris (pH 7.0); 1 mM EDTA; 1 mM DTT, 0.01 mM PMSF), 60 column volumes of wash buffer A with 1 M NaCl, and followed by folate elution (5 mM folate; 32 mM Tris (pH 9.0); 1 mM EDTA; 1 mM DTT, 0.01 mM PMSF). 8 ml fractions were collected at a flow rate of 3 mi/min and an aliquot of each fraction (10 µL) was assayed for protein concentration with the Bradford dye reagent (Biorad). Fractions containing more than 0.1 mg/ml of protein were analyzed by 12% SDS-PAGE, and DHFR activities were determined as described (Stone & Morrison, 1982, *Biochem.*, 21:3757–65; Morrison & Stone, 1988, *Biochem.*, 27:5499–5506). The standard DHFR assay mixture contained 50 µM DHF, 100 µM NADPH and 1 mM DTT in MTEN buffer (50 mM 2-morpholinoethanesulfonic acid, 25 mM tris(hydroxymethyl)aminomethane, 25 mM ethanolamine, and 100 mM NaCl (pH 7.0)), and the enzyme in a final volume of 1.0 ml. The reaction was started by the addition of DHF. Fractions containing pure Hint-DHFR fusion proteins were pooled and concentrated to 2 mg/ml. A 2.5-ml protein solution was further purified and exchanged with buffer A without PMSF by Sephadex G-25 PD-10 desalting column (Amersham Pharmacia).

Purified Hint-DHFR fusion proteins were dialyzed against thrombin-cleavage buffer (50 mM Tris (pH 8.0); 0.1 M NaCl; 2.5 mM CaCl$_2$) and digested with human thrombin (Sigma) at 4° C. for 19 h at a concentration of 8 U/mg protein. To separate Hint hydrolases from DHFR domains, reaction mixtures were applied to a 10 ml AMP-agarose affinity column (Sigma) and washed with 16 column volumes of buffer A with 1 M NaCl, 4 column volumes of buffer A, and eluted with adenosine buffer (2 mM adenosine, 20 mM Tris (pH 7.0); 1 mM EDTA; 1 mM DTT). 8 ml fractions were collected at a flow rate of 3 ml/min and aliquots from each fraction (10 µL) were used to determine the protein concentration. Fractions containing more than 0.1 mg/ml of protein were analyzed by 18% SDS-PAGE. Fractions containing pure Hint protein were pooled and concentrated to 2.6 mg/ml.

Rabbit Hint was purified by AMP-agarose affinitiy chromatography as previously described (Bieganowski et al, 2002, *J. Biol. Chem.*, 277:10852–60; Gilmour et al, 1997, *Biochem. J.*, 326:471–77) except that expression was performed with the *E. coli* hinT deletion mutant described in this study.

Example 6

Phosphoramidase Activities for Purified Proteins with Three Substrates

Five recombinant purified proteins were tested with three commercial available compounds (Sigma): AMP-NH$_2$, adenosine 5'-monophosphomorpholidate (AMP-Mor), and guanosine 5'-monophosphomorpholidate (GMP-Mor) (FIG. 1). The compounds (10 mM) were incubated with proteins (2.5–10 μg) in the reaction buffer (500 μL, 0.5 mM MgCl$_2$, 20 mM HEPES (pH 7.2)) at 22° C. for intervals of 36 and 66 min. The reactions were quenched by adding 5 M NaOH (20 μL), followed by snap freezing in a dry ice/acetone slush bath, and lyophilized. The sample preparation for $^{31}$P NMR measurement was as described above for the cell-lysate experiment except that the pH was adjusted by the addition of 12 μL 6 M HCl before NMR spectra were collected.

Example 7

Gel Filtration

The apparent molecular weights of recombinant purified E. coli hinT and E. coli hinT-DHFR fusion protein were analyzed by analytical gel filtration chromatography on a Superdex G-75 size exclusion column (Amersham Pharmacia) and the proteins were eluted with P500 buffer (0.5 M NaCl, 50 mM potassium phosphate, 1 mM EDTA (pH 7.0)). The retention time of each protein was monitored by in line U.V. and fluorescence detectors. Standard curves were created using a molecular weight calibration kit (Amersham Pharmacia). The size standards used were blue dextran (200 kDa), albumin (66 kDa), carbonic anhydrase (29 kDa), cytochrome C (12.4 kDa), and aprotinin (6.5 kDa).

Example 8

E. coli Cell Lysates Possess Adenosine Phosphoramidase Activity

Figure 2:
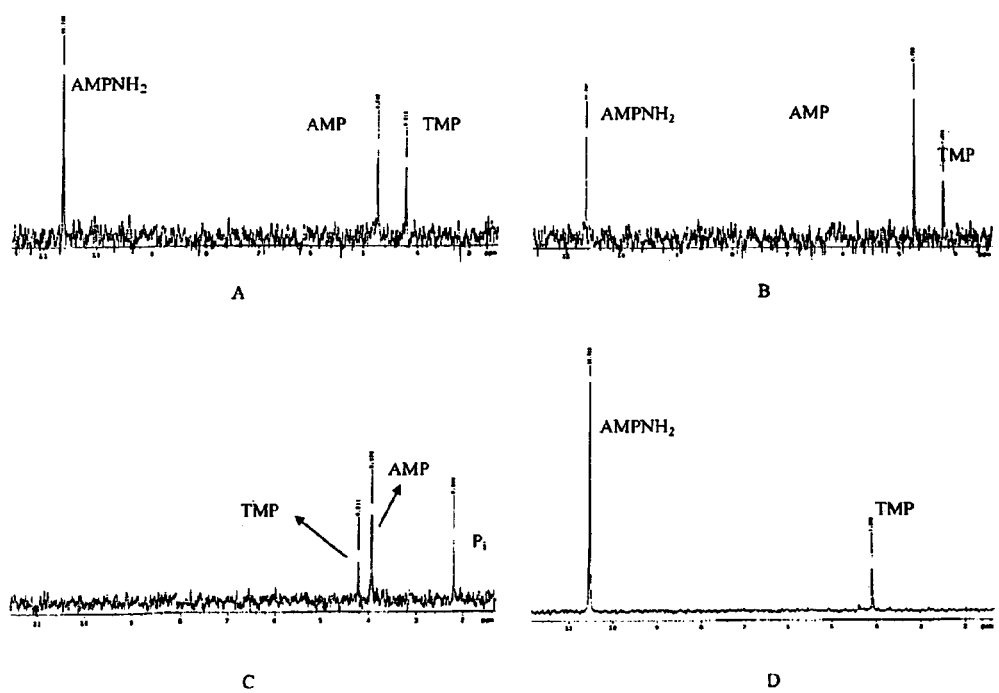
FIG. 2 is a $^{31}$P NMR spectra of adenosine monohosphoramidase activity in *E. coli*.

Tuner(DE3)pLacI, a modified E. coli BL21 strain, was used to determine phosphoramidase activity in cell lysates. At pH 7.0, the AMP-NH$_2$ hydrolysis rate by E. coli cell lysates was 76.3 (±20.9) nmol mg$^{-1}$ min$^{-1}$; data were averaged for incubation time intervals of 15 min, and 30 min (FIGS. 2A and 2B). The 12 h incubation reaction showed complete hydrolysis of AMP-NH$_2$ to AMP, as well as limited further cleavage of AMP into inorganic phosphate (Pi) and adenosine. The production of Pi may be the result of E. coli phosphatases or chemical hydrolysis (FIG. 2C). To verify that the formation of AMP was due to an enzymatic process and not chemical hydrolysis, a control experiment was performed by incubating 10 mM AMP-NH$_2$ (pH 2.0) in buffer at 37° C. for 12 h (FIG. 2D). The pH 2.0 test conditions were chosen due to the acid lability of phosphorous-nitrogen bond (P—N bond). Clear AMP-NH$_2$ and TMP signals were visible by $^{31}$PNMR with no detectable AMP or P$_i$, confirming that AMP-NH$_2$ is stable at pH 2.0 for at least 12 h.

Example 9 hinT is the Only Bacterial Source of Adenosine Monophosphoramidase Activity

To determine if E. coli hinT is solely responsible of the observed lysates' phosphoramidase activity, a mutant strain, BB1, in which the hinT gene was replaced with the chloramphenicol resistance marker, was constructed. The phosphoramidase activities of the wild-type E. coli BL21 Star strain and the mutant strain lysates were determined (Table 3). When using AMP-NH$_2$ as a substrate, the specific activity of BL21 Star WT cell lysates was found to be 20.1 (±7.7) nmol mg$^{-1}$ min$^{-1}$. However, no AMP formation could be observed with lysates derived from the hinT deletion strain, BB1. (Table 2). Therefore, the adenosine phosphoramidase activity observed for E. coli cell lysates appears to be totally dependent on hinT.

TABLE 3

Phosphoramidase activities of BB2-1 and BL21 Star WT cell lysates

| Cell lysates | AMPNH$_2$ Integration | AMP Integration | Pi | Protein (mg) | Time (min) | Specific Activity (nmol mg$^{-1}$ min$^{-1}$) | Average (nmol mg$^{-1}$ min$^{-1}$) |
|---|---|---|---|---|---|---|---|
| BL21 Star (WT) | 12 | NA | 0 | 0.2 | 30 | NA | |
| BL21 Star (WT) | 10.47 | 0.51 | 0 | 0.5 | 30 | 15.5 | 20.95 ± 7.71 |
| BL21 Star (WT) | 7.53 | 1.71 | 0 | 0.5 | 70 | 26.4 | |
| BL21 Star (WT) | 0 | 7.32 | 1.54 | 0.5 | 1380 | NA | |
| BB2-1 (-HINT) | 8.4 | 0 | 0 | 0.2 | 30 | 0 | 0 |
| BB2-1 (-HINT) | 10.94 | 0 | 0 | 0.5 | 30 | 0 | |
| BB2-1 (-HINT) | 16.2 | 0 | 0 | 0.5 | 70 | 0 | |
| BB2-1 (-HINT) | 8.85 | 0 | 0 | 0.5 | 1380 | 0 | |

Example 10

Nucleoside and Leaving Group Specificity of Bacterial and Mammalian Hint Hydrolases Both E. coli hinT and human Hint1 were purified to homogeneity as DHFR fusion proteins by MTX affinity chromatography. Removal of the DHFR affinity handle by thrombin digestion and AMP affinity chromatography afforded the purified recombinant enzymes. Based on the $^{31}$P NMR assay that was developed, it was found that E. coli hinT and human Hint1 are adenosine phosphoramidases with specific activities of 526 (±27) and 196 (±33) nmol nmol$^{-1}$ min$^{-1}$, respectively.

To evaluate the substrate specificity with respect to the different purine nucleoside phosphoramidates, the purified Hint hydrolases were evaluated with AMP-Mor and GMP-Mor (FIG. 1). AMP-Mor has previously been shown to be a reasonable substrate for rabbit Hint1 and yeast Hnt1. All three Hint hydrolases were fully capable of utilizing both compounds as substrates with a 2-fold preference for the GMP-Mor. Hydrolysis rates for the three Hint hydrolases with each substrate are summarized in Table 2.

Example 11

Apparent Molecular Weight of *E. coli* HINT

Both *E. coli* hinT and *E. coli* hinT-DHFR fusion protein were subjected to analytical gel filtration on a G-75 size exclusion column (Amersham Pharmacia). *E. coli* hinT was eluted at 24.6 min, which, based on the molecular weight standard curve, corresponded to a calculated molecular weight of 27.4 kDa. The fusion protein was eluted at 19.0 min, corresponding to a calculated molecular weight of 69.9 kDa. The theoretical molecular weight of the *E. coli* hinT and hint-DHFR fusion protein are 13641.7 Da and 34175.9 Da, respectively. The theoretical molecular weights of the dimeric species, 27.3 and 68.4 kDa, respectively, correspond closely to the experimental observation, strongly indicating the formation of a stable homodimer in solution.

Example 12 hinT is Required for Growth Under High Saline Conditions

The *E. coli* hinT knockout strain BB3 was transformed with either a control plasmid (hinTΔ pACYC) a plasmid expressing *E. coli* hinT (pACYC-hinT), or a plasmid expressing the catalytically inactive HINT His-101 to Ala mutant (pACYC-hinT-H101A).

When cultures were grown under high salt conditions (LB-agar media containing 0.9 M NaCl), colonies were only observed for BB3 cells transformed with pACYC-hinT (hinTΔ pACYC-hinT). In either case, the amount of expressed and soluble wild type or mutant hinT by BB3 cells was nearly identical. Consequently, expression of a catalytically-active Hint hydrolase is required by *E. coli* for growth under saline conditions.

Example 13

Phosphoramidase Fluorescence Assay

Figure 5:
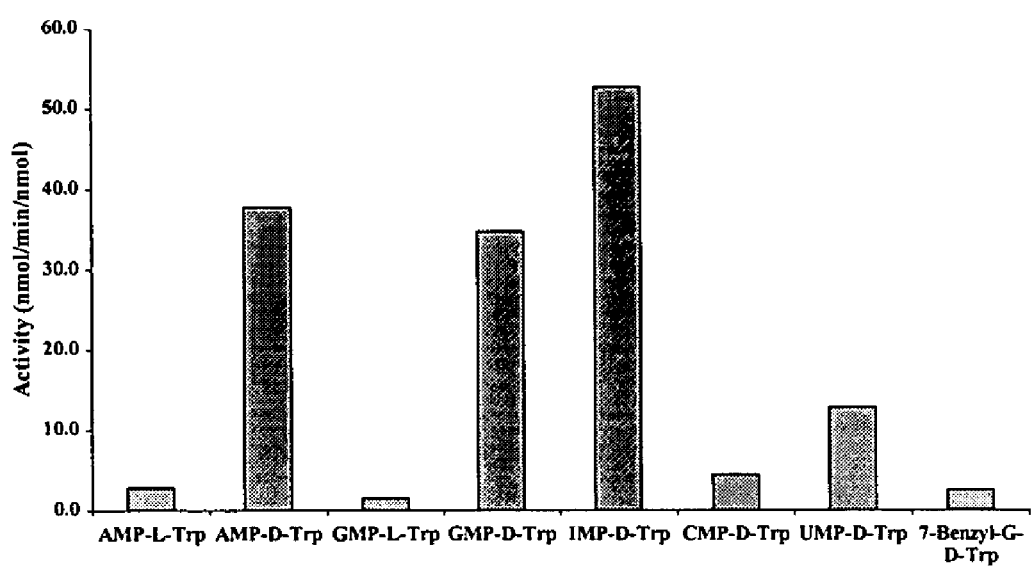
FIG. 5 is a graph showing a substrate preference screen with fluorescent substrates.

The fluorescence of tryptophan (ex, 280 nm, em 360 nm) can be quenched when covalently attached to a nucleoside monophosphate, and nucleoside phosphoramidates of D- and L-tryptophan and tryptamine are excellent fluorescent substrates for hHINT1. Typically, after measurement of initial substrate fluorescence, hHINT1 was added to the reaction solution (HEPES buffer, pH 7.2, 25° C.) and the change in fluorescence over 2 min was determined by converting the slope into µM of substrate hydrolyzed per µg of enzyme per min with a standard curve. As can be seen in FIG. 5, the phosphoramidates containing D-tryptophan were preferred by hHINT1 over those containing L-tryptophan by 6- to 10-fold. Based on the generation of chimeric polypeptides between the hHINTI and the hinT of *E. coli*, the preference for D enantiomers by the human HINT1 polypeptide is likely conferred by the C-terminus amino acids (e.g., the C-terminus 5, 6, 5 7, 8, 9, 10, or 11 amino acids) of the hHINT1 enzyme. The activity of hHINT1 with guanosine monophosphate (GMP) D-tryptophan phosphoramidate was approximately 7-fold greater than that for 7-benzyl guanosine monophosphate (7-Bn GMP), but nearly identical to that for GMP L-tryptophan. In addition, both D-tryptophan phosphoramidates of cytosine and uridine were substrates. Initial rates were determined during the first 10–20% of the reaction for variable substrate concentrations. The Michaelis-Menten constants, $k_{cat}$ and $K_m$, for selected nucleoside phosphosphoramidates have been determined. (Table 4). As observed in the initial screening assay, for phosphoramidates containing L-tryptophan, hHINT1 has a 7-fold greater preference for AMP phosphoramidates of L-tryptophan than GMP.

TABLE 4

Steady-State Kinetic Parameters for hHINT1 and L-Tryptophan Phosphoramidates

| Substrate | Km (µM) | k cat (s⁻¹) | k cat/Km (M⁻¹ s⁻¹) |
|---|---|---|---|
| AMP-TrpCOOMe | 31.1 ± 9.2 | 3.02 | 97,000 |
| GMP-Trp COOMe | 101 ± 27 | 1.42 | 14,100 |
| GMP-Trp CONH₂ | 28.3 ± 5.9 | 0.44 | 15,400 |

In addition, the Michaelis-Menten constants, $k_{cat}$ and $K_m$, for selected nucleoside phosphoramidates were determined for both human Hint1 and *E. coli* hinT (Table 5).

TABLE 5

Steady-State Kinetic Parameters of hHINT1 and *E. coli* hinT and various Phosphoramidates

| | $K_{cat}$ (s⁻¹) | | Km (µM) | | $K_{cat}$/Km (mM⁻¹s⁻¹) | |
|---|---|---|---|---|---|---|
| Compounds | Human Hint1 | *E. coli* hinT | Human Hint1 | *E. coli* hinT | Human Hint1 | *E. coli* hinT |
| GMP-Tryptamine | 2.09 ± 0.16 | 3.45 ± 0.3 | 0.243 ± 0.03 | 5.34 ± 0.69 | 8549 | 647 |
| AMP-Tryptamine | 2.05 ± 0.27 | 4.07 ± 0.11 | 0.25 ± 0.05 | 5.03 ± 0.21 | 8205 | 810 |
| IMP-Tryptamine | 2.53 ± 0.09 | 3.89 ± 0.18 | 0.71 ± 0.03 | 13.72 ± 0.67 | 3583 | 283 |
| Ara-AMP-Tryptamine | 0.85 ± 0.1 | 0.95 ± 0.17 | 0.79 ± 0.11 | 34.55 ± 5.64 | 1095 | 27.4 |
| UMP-Tryptamine | 1.85 ± 0.29 | 1.63 ± 0.22 | 1.42 ± 0.25 | 25.07 ± 3.56 | 1309 | 65 |

TABLE 5-continued

Steady-State Kinetic Parameters of hHINT1 and E. coli hinT and various Phosphoramidates

| Compounds | $K_{cat}$ (s$^{-1}$) | | $K_m$ (μM) | | $K_{cat}/K_m$ (mM$^{-1}$s$^{-1}$) | |
|---|---|---|---|---|---|---|
| | Human Hint1 | E. coli hinT | Human Hint1 | E. coli hinT | Human Hint1 | E. coli hinT |
| CMP-Tryptamine | 0.97 ± 0.11 | 0.45 ± 0.04 | 1.74 ± 0.22 | 30.1 ± 2.39 | 558 | 15 |
| TMP-Tryptamine | 0.044 ± 0.01 | 0.014 ± 0.001 | 26.13 ± 2.78 | 35.91 ± 2.27 | 1.7 | 0.4 |
| GMP-L-TrpCOOMe | 0.057 ± 0.02 | 1.96 ± 0.12 | 28.6± | 19.88 ± 2.2 | 2.0 | 98.8 |
| GMP-D-TrpCOOMe | 0.29 ± 0.02 | 1.75 ± 0.05 | 3.27 ± 0.58 | 21.33 ± 1.21 | 88.7 | 82.0 |
| GMP-Tryptamine | 2.09 ± 0.16 | 3.45 ± 0.3 | 0.243 ± 0.03 | 5.34 ± 0.69 | 8549 | 647 |
| AMP-Tryptamine | 2.05 ± 0.27 | 4.07 ± 0.11 | 0.25 ± 0.05 | 5.03 ± 0.21 | 8205 | 810 |
| AMP-lysine[a] | 0.234 ± 0.011 | ND | 0.472 ± 0.057 | ND | 496 | ND |
| AMPNH$_2$[b] | 0.2 | ND | 0.068 | ND | 2941 | ND |

[a]Krakowiak and Brenner J. Biol. Chem. 2004, 279, 18711;
[b]Bieganowski and Brenner J. Biol. Chem. 2002, 277, 10852.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of screening nucleoside phosphoramidate compounds for cleavage by a nucleoside phosphoramidase enzyme, comprising:
   contacting a nucleoside phosphoramidate test compound with a purified nucleoside phosphoramidase enzyme, wherein the nucleoside phosphoramidase is encoded by a nucleic acid molecule comprising the sequence shown in SEQ ID NO:1, SEQ ID NO:2 or SEQ ID NO:3 or a nucleic acid molecule having at least 95% sequence identity to the sequence shown in SEQ ID NO:1, SEQ ID NO:2 or SEQ ID NO:3; and
   determining whether or not the nucleoside phosphoramidase enzyme cleaved the nucleoside phosphoramidate test compound.

2. The method of claim 1, wherein the nucleoside phosphoramidate test compound is a purine phosphoramidate.

3. The method of claim 2, wherein the purine phosphoramidate is a guanine phosphoramidate.

4. The method of claim 1, wherein the nucleoside phosphoramidate test compound is a D enantiomer.

5. The method of claim 1, wherein the determining step uses NMR spectroscopy.

6. The method of claim 1, wherein the determining step uses a fluorescent assay.

7. A method of screening nucleoside phosphoramidase enzymes for the ability to cleave a nucleoside phosphoramidate compound, comprising:
   contacting a purified nucleoside phosphoramidase test enzyme with a nucleoside phosphoramidate, wherein the nucleoside phosphoramidase is encoded by a nucleic acid molecule comprising the sequence shown in SEQ ID NO:1, SEQ ID NO:2 or SEQ ID NO:3 or a nucleic acid molecule having at least 95% sequence identity to the sequence shown in SEQ ID NO:1, SEQ ID NO:2 or SEQ ID NO:3, and
   determining whether or not the nucleoside phosphoramidase enzyme cleaved the nucleoside phosphoramidate test compound.

8. The method of claim 7, wherein the nucleoside phosphoramidase enzyme is a chimeric enzyme.

* * * * *

SEQUENCE LISTING

<160> NUMBER OF SEQ ID NOS: 6

<210> SEQ ID NO 1
<211> LENGTH: 549
<212> TYPE: DNA
<213> ORGANISM: Homo sapiens

<400> SEQUENCE: 1

```
atggcggagg aacaggtgaa ccgcagcgcc ggcctggccc ccgactgtga ggcctcggcg      60
actgcagaaa ctacggtttc ctcagtgggg acctgtgaag ccgctgccaa gtcaccagag     120
cccaaggact acgacagcac ctgcgtgttc tgccggatcg cggggcggca ggacccgggc     180
accgaactcc tgcactgcga gaatgaggac ctaatttgct tcaaagatat caaaccagca     240
gcaactcatc attatcttgt ggtgccaaag aagcatattg gaaactgcag aactctaagg     300
aaagatcaag tagaactggt tgagaacatg gtaactgttg gaaaaaccat tcttgaaaga     360
aataatttca ctgacttcac gaatgtgagg atgggttttc atatgccacc attctgttcc     420
atttcccact tgcaccttca tgttctggca ccagtggatc agcttggctt cttatccaag     480
ttggtttata gagtcaattc ctattggttt atcacagctg atcacttgat tgaaaaacta     540
agaacatga                                                              549
```

<210> SEQ ID NO 2
<211> LENGTH: 549
<212> TYPE: DNA
<213> ORGANISM: Homo sapiens

<400> SEQUENCE: 2

```
atggcggagg aacaggtgaa ccgcagcgcc ggcctggccc ccgactgtga ggcctcggcg      60
actgcagaaa ctacggtttc ctcagtgggg acctgtgaag ccgctggcaa gtcaccagag     120
```

-continued

```
cccaaggact acgacagcac ctgcgtgttc tgccggatcg cggggcggca ggacccgggc    180
accgaactcc tgcactgcga gaatgaggac ctaattttgct tcaaagatat caaaccagca   240
gcaactcatc attatcttgt ggtgccaaag aagcatattg gaaactgcag aactctaagg    300
aaagatcaag tagaactggt tgagaacatg gtaactgttg aaaaaccat tcttgaaaga     360 aataatttca ctgacttcac gaatgtgagg atgggttttc atatgccacc attctgttcc    420
atttcccact tgcaccttca tgttctggca ccagtggatc agcttggctt cttatccaag    480
ttggtttata gagtcaattc ctattggttt atcacagctg atcacttgat tgaaaaacta    540
agaacatga                                                            549
```

<210> SEQ ID NO 3
<211> LENGTH: 360
<212> TYPE: DNA
<213> ORGANISM: Escherichia coli

<400> SEQUENCE: 3

```
gtggcagaag aaactatatt cagcaaaatt attcgtcgtg agatcccctc cgatatcgtc    60
taccaggatg atctggtaac ggcgtttcgc gatatttcgc cgcaagcgcc aacgcatatt    120
ctgatcattc cgaatatcct cattccgact gtgaacgacg tctcagctga gcatgagcag    180
gcgctgggac gcatgatcac cgtagcggca aaaattgctg agcaagaagg tattgccgaa    240
gatggctatc gtctgatcat gaataccaac cgccatggcg acaagaggt ttaccacatc     300 catatgcact tgttgggtgg ccgtccgctg ggaccaatgc tggcgcataa aggtctgtaa    360
```

<210> SEQ ID NO 4
<211> LENGTH: 182
<212> TYPE: PRT
<213> ORGANISM: Homo sapiens

<400> SEQUENCE: 4

```
Met Ala Glu Glu Gln Val Asn Arg Ser Ala Gly Leu Ala Pro Asp Cys
 1               5                  10                  15

Glu Ala Ser Ala Thr Ala Glu Thr Thr Val Ser Ser Val Gly Thr Cys
            20                  25                  30

Glu Ala Ala Ala Lys Ser Pro Glu Pro Lys Asp Tyr Asp Ser Thr Cys
        35                  40                  45

Val Phe Cys Arg Ile Ala Gly Arg Gln Asp Pro Gly Thr Glu Leu Leu
    50                  55                  60

His Cys Glu Asn Glu Asp Leu Ile Cys Phe Lys Asp Ile Lys Pro Ala
65                  70                  75                  80

Ala Thr His His Tyr Leu Val Val Pro Lys Lys His Ile Gly Asn Cys
                85                  90                  95

Arg Thr Leu Arg Lys Asp Gln Val Glu Leu Val Glu Asn Met Val Thr
            100                 105                 110

Val Gly Lys Thr Ile Leu Glu Arg Asn Asn Phe Thr Asp Phe Thr Asn
        115                 120                 125

Val Arg Met Gly Phe His Met Pro Pro Phe Cys Ser Ile Ser His Leu
    130                 135                 140

His Leu His Val Leu Ala Pro Val Asp Gln Leu Gly Phe Leu Ser Lys
145                 150                 155                 160

Leu Val Tyr Arg Val Asn Ser Tyr Trp Phe Ile Thr Ala Asp His Leu
                165                 170                 175

Ile Glu Lys Leu Arg Thr
            180
```

180

<210> SEQ ID NO 5
<211> LENGTH: 182
<212> TYPE: PRT
<213> ORGANISM: Homo sapiens

<400> SEQUENCE: 5

Met Ala Glu Glu Gln Val Asn Arg Ser Ala Gly Leu Ala Pro Asp Cys
 1               5                  10                  15

Glu Ala Ser Ala Thr Ala Glu Thr Thr Val Ser Ser Val Gly Thr Cys
             20                  25                  30

Glu Ala Ala Gly Lys Ser Pro Glu Pro Lys Asp Tyr Asp Ser Thr Cys
         35                  40                  45

Val Phe Cys Arg Ile Ala Gly Arg Gln Asp Pro Gly Thr Glu Leu Leu
     50                  55                  60

His Cys Glu Asn Glu Asp Leu Ile Cys Phe Lys Asp Ile Lys Pro Ala
 65                  70                  75                  80

Ala Thr His His Tyr Leu Val Val Pro Lys Lys His Ile Gly Asn Cys
                 85                  90                  95

Arg Thr Leu Arg Lys Asp Gln Val Glu Leu Val Glu Asn Met Val Thr
            100                 105                 110

Val Gly Lys Thr Ile Leu Glu Arg Asn Asn Phe Thr Asp Phe Thr Asn
        115                 120                 125

Val Arg Met Gly Phe His Met Pro Pro Phe Cys Ser Ile Ser His Leu
    130                 135                 140

His Leu His Val Leu Ala Pro Val Asp Gln Leu Gly Phe Leu Ser Lys
145                 150                 155                 160

Leu Val Tyr Arg Val Asn Ser Tyr Trp Phe Ile Thr Ala Asp His Leu
                165                 170                 175

Ile Glu Lys Leu Arg Thr
            180

<210> SEQ ID NO 6
<211> LENGTH: 119
<212> TYPE: PRT
<213> ORGANISM: Escherichia coli

<400> SEQUENCE: 6

Met Ala Glu Glu Thr Ile Phe Ser Lys Ile Ile Arg Arg Glu Ile Pro
 1               5                  10                  15

Ser Asp Ile Val Tyr Gln Asp Asp Leu Val Thr Ala Phe Arg Asp Ile
             20                  25                  30

Ser Pro Gln Ala Pro Thr His Ile Leu Ile Pro Asn Ile Leu Ile
         35                  40                  45

Pro Thr Val Asn Asp Val Ser Ala Glu His Glu Gln Ala Leu Gly Arg
     50                  55                  60

Met Ile Thr Val Ala Ala Lys Ile Ala Glu Gln Glu Gly Ile Ala Glu
 65                  70                  75                  80

Asp Gly Tyr Arg Leu Ile Met Asn Thr Asn Arg His Gly Gly Gln Glu
                 85                  90                  95

Val Tyr His Ile His Met His Leu Leu Gly Gly Arg Pro Leu Gly Pro
            100                 105                 110

Met Leu Ala His Lys Gly Leu
        115